United States Patent [19]

Korous et al.

[11] 4,044,062
[45] Aug. 23, 1977

[54] HYDROCARBON SEPARATION

[75] Inventors: Donald J. Korous, Maywood; Richard W. Neuzil, Downers Grove, both of Ill.

[73] Assignee: Universal Oil Products Company, Des Plaines, Ill.

[21] Appl. No.: 136,199

[22] Filed: Apr. 21, 1971

[51] Int. Cl.$^2$ ............................................. C07C 7/13
[52] U.S. Cl. ........................... 260/674 SA; 208/310 Z
[58] Field of Search ........................... 208/310, 310 Z; 260/674 SA, 674 A

[56] References Cited

U.S. PATENT DOCUMENTS

| 3,114,782 | 12/1963 | Fleck et al. | 260/674 |
| 3,126,425 | 3/1964 | Eberly et al. | 260/674 |

Primary Examiner—Delbert E. Gantz
Assistant Examiner—C. E. Spresser
Attorney, Agent, or Firm—James R. Hoatson, Jr.; Robert W. Erickson; William H. Page, II

[57] ABSTRACT

A process for the separation of a para-isomer from a hydrocarbon feed stock containing alkyl-aromatic hydrocarbons having more than eight carbon atoms per molecule which employs a crystalline aluminosilicate adsorbent containing a particular cation or cations to selectively adsorb either a para-, meta-, or ortho- isomer from the feed stock. A feed stock contacts an adsorbent which allows one or more isomers from the feed stock to be selectively adsorbed by the adsorbent. The selectively adsorbed component is thereafter recovered from the adsorbent in a more pure form as compared to the other isomers in the feed stock. The process can be performed in both the liquid or vapor phase.

5 Claims, No Drawings

1

HYDROCARBON SEPARATION

BACKGROUND OF THE INVENTION

1. Field of the Invention

The field of art to which the claimed invention pertains is hydrocarbon separation. More specifically, the claimed invention relates to the separation of a monoaromatic hydrocarbon using a solid adsorbent which selectively removes one or more of the aromatic components from the feed stock.

2.

Description of the Prior Art

It is known in the separation art that certain crystalline aluminosilicates can be used to separate individual hydrocarbons from mixtures thereof. In particular, the separation of normal paraffins from branched chained paraffins can be accomplished by using the Type A zeolites which have pore openings from 3 to about 5 Angstroms. These adsorbents allow a separation based on the physical size differences in the molecules by allowing the smaller or normal hydrocarbons to be passed into the cavities within the crystalline aluminosilicate adsorbent, while excluding the larger or branched chain molecules. Other separations have been recognized using the larger pore diameter zeolites — namely, the type X or type Y structured zeolites to separate xylene isomers or the polynuclear aromatics such as the alkyl substituted naphthalenes.

The present invention relates to the separation of mono-nuclear aromatic hydrocarbons having more than eight carbons atoms per molecule and necessarily exclude the teachings specifically directed towards xylene separation.

We have found that type X and type Y structured crystalline aluminosilicate zeolites which contain certain selected cations provide selectivities which preferably allow one or more isomer from a group of isomers to be adsorbed by the adsorbent.

SUMMARY OF THE INVENTION

The attached claims can be summarized as encompassing a process for the separation of $C_9$ and greater mono-nuclear aromatic hydrocarbons having bi-alkyl substitutions by using a specific type X or type Y structured cyrstalline aluminosilicate adsorbent to selectively adsorb one or more of the feed stock isomers and thereafter recovering selectively adsorbed components.

The utility of the process of this invention is generally recognized. In refinery processing the ability to separate various isomers in concentrated streams allows the refiner to make feed stocks available for other processes and to selectively remove more valuable isomers from a mixture containing them.

PREFERRED EMBODIMENTS

Adsorbents which can be used in the process of this invention include the synthetically prepared type X and type Y structured crystalline aluminosilicates which contain selected cations at the exchangeable cationic sites within the crystalline structure. The term "type X structured" or "type Y structured" zeolites include the specific type X and type Y zeolites claimed in U.S. Pat. Nos. 2,882,244 and 3,130,007 which contain sodium or other cations present at the ion exchangeable sites within the zeolites. That term also includes both single and cation combinations as later described herein.

The type X and type Y structured zeolites may contain binder materials in order to physically hold the adsorbent together in a particle size useful for separation. The amount of binder can vary from a few percent up to 25 or more weight percent binder material. The binder material can be a clay or other compound which is well known in the art and preferably inert with respect to catalysis and separation ability.

Both the natural and synthetic aluminosilicates may be used as absorbents in the present invention. A crystalline zeolitic aluminosilicate encompassed by the present invention for use as an adsorbent includes aluminosilicate cage structures in which the alumina and silica tetrahedra are intimately connected with each other in an open three-dimensional crystalline network. The tetrahedra are cross-linked by the sharing of oxygen atoms. The spaces between the tetrahedra are occupied by water molecules prior to dehydration. Subsequent partial or total dehydration results in crystals interlaced with channels of molecular dimensions. Thus, the crystalline aluminosilicates are often referred to as molecular sieves. In the hydrated form, the crystalline aluminosilicates may be represented by the formula represented in equation 1, $$M_{2/n}O:Al_2O_3:wSiO_2:yH_2O \tag{1}$$

where M is a cation which balances the electrovalence of the tetrahedra, $n$ represents the valence of the cation, $w$ represents the mols of $SiO_2$, and Y, the mols of water. The cations may be any one of a number of cations such as for example the alkali metal cations or the alkaline earth cations or other selected cations.

Crystalline aluminosilicates which find use as adsorbents in the process of this invention possess relatively well-defined pore structures. The exact type aluminosilicate is generally referred to by the particular silicaalumina ratio and the pore dimensions of the cage structures.

The type X structured zeolite can be represented in terms of the mol ratio of oxides as represented in the following equation 2, $$0.9\pm0.2M_{2/n}O:Al_2O_3:2.5\pm0.5SiO_2:yH_2O \tag{2}$$

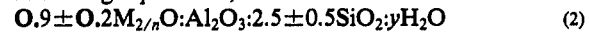

where M represents at least 1 cation having a valence of not more than 3, $n$ represents the valence of M, and $y$ is a value up to about 8 depending upon the identity of M and the degree of hydration of the crystal. Zeolite type X is described in U.S. Pat. No. 2,882,244.

The type Y structured zeolite may be represented in the terms of the mol ratio of oxides for the sodium form as represented in the following equation 3, $$0.9\pm0.2Na_2O:Al_2O_3:wSiO_2:yH_2O \tag{3}$$

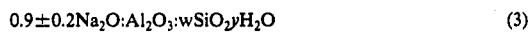

The exchangeable cationic sites for the type X and Y zeolites, in general, can be defined as represented in equation (1) above as M. Cationic exchange or base exchange methods are generally known to those familiar with the field of crystalline aluminosilicate production and are generally performed by contacting a zeolite with an aqueous solution of soluble salts of the cations or cation desired to be exchanged on the sieve. The desired degree of cation exchange is allowed to take place before the sieves are removed from the aqueous solution and dried to a desired water content. It is contemplated that in cationic exchange or base exchange methods that the cation exchange may take place using individual solutions of desired cations to be placed on the molecular sieve or can use exchange solutions containing mixtures of the cations which are desired to be exchanged onto the crystalline aluminosilicate zeolite.

The type X and Y structured zeolite adsorbents containing at their exchangeable cationic sites cations from the group of potassium, rubidium, cesium, barium, copper, silver, lithium, sodium, beryllium, magnesium, calcium, strontium, cadmium, cobalt, nickel, manganese and zinc or combination thereof are preferred for use in the separation process herein disclosed when the preferred adsorption of a para-isomer from its isomeric mixtures is to be performed. It is, therefore, preferred to employ type X or type Y zeolite adsorbents containing both cations from the former group of cations and cations from the latter group of cations to effectively separate para-isomers from a mixture containing para-, meta-, and ortho-isomers. The type X and Y zeolites which demonstrated the best selectivities for para-isomers separation and which are preferred are those zeolites containing both barium and potassium cations, or potassium and beryllium cations, or potassium and magnesium cations, or rubidium and barium cations, or cesium and barium cations, or potassium and rubidium cations or potassium and cesium cations.

Feed stocks which can be utilized in the process of this invention include bi-alkyl substituted mono-cyclic aromatics having anywhere from nine up to about eighteen carbon atoms per molecule. Specifically, the feed stocks which can be used in the process of this invention are characterized by the formula shown in equation (4) below.

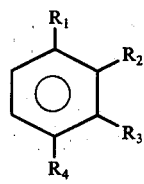

(4)

Wherein, $R_1$, $R_2$, $R_3$ and $R_4$ are selected from the group of alkyl chains in a manner to allow an essentially bi-alkyl substitution at either ortho-, meta-, or para- isomer positions. The R substitutional groups can include alkyl groups ranging from methyl substitution groups up to and including chains having 11 or less carbon atoms per molecule. The alkyl side chains can be both normal and branched in nature and are preferably saturated chains. It is believed that unsaturation of a portion of either or both of the alkyl chains in the feed stocks will make the compounds less susceptible to separation by their isomer configuration making the separation more dependent on olefinicity than isomer configuration.

Specific representative compounds which can be utilized as feedstocks in the process include those feedstocks containing the various isomers of methylethylbenzene, diethylbenzene, isopropyltoluene, the methylpropylbenzenes, ethylpropylbenzenes, methylbutylbenzenes, ethylbutylbenzenes, dipropylbenzenes, methylpentylbenzene, etc., and combinations thereof. The above list ony represents a small fraction of feed stocks which can be separated by selections of specific adsorbents utilized in this process.

The feed stocks which are separated in this process can be separated according to their configuration depending whether they are of a para-, meta- or ortho-isomer construction. It is contemplated that feed stocks containing mixtures of more than one class of isomers — namely, $C_9$ isomers in mixture with $C_{10}$ or $C_{11}$ isomers, that one of the isomers of the higher molecular weight component of the feed stock may be more selectively held by the adsorbent than different type isomer from a lower molecular weight compound solely on the basis of molecular weight and not because of isomer configuration differences. It is therefore preferred in the process of this invention to utilize as feed stocks only a single class of isomers, that is, isomers having an equal number of carbon number per molecule. It is more preferable to use isomers having as their only differences the location of the alkyl substituted groups in a para-, meta- or ortho-position. The alkyl structures should preferably be the same for each isomer of a class. In some instances an isomer may have alkyl chains which are both normal or branched or one branched and one normal.

The feed stocks may contain small quantities of straight or branched chain paraffins, cyclo-paraffins or olefinic materials. It is preferable to have these quantities at a minimum amount in order to prevent contamination of products from this process by materials which are not selectively adsorbed or separated by the adsorbent. Preferably the above-mentioned contaminants should be less than about 20% of the volume feed stock passed into the process.

Desorbents which can be used in the process of this invention should be materials that are easily separable from the feed mixture that is passed into the process. In desorbing the preferentially adsorbed component of the feed both desorbent and the described feed component are removed from the adsorbent in admixture. Without a method of separation in these two materials, the purity of the selectively adsorbed component of the feedstock would not be very high since it would be diluted with desorbent. It is contemplated that a desorbent that is of a different boiling range than the feed mixture used should be used in this process. The use of a desorbent of a different boiling range allows a simple separation by fractionation or other methods to remove desired feed components from the desorbent and allow reuse of the desorbent in the process. Specific desorbents which can be used in the process of this invention include benzene, toluene, esters, alcohols, cyclic dienes, the ketones or a feed component material which has a significantly different boiling range than a boiling range of the feed stock used. It is contemplated that desorbents having both higher and lower boiling points in the feed stocks can be utilized. Gaseous materials such as nitrogen, hydrogen, methane, ethane, etc., can also be used as a desorbent materials where the desorbent operation takes place by a purging step.

Adsorption and desorption conditions can be both liquid and vapor phase. The liquid phase operation are preferred because of the lower temperature requirements and the slightly improved selectivities associated with the lower temperatures. Temperature ranges which can be used in adsorption can vary from about 40° C. up to about 250° C. Pressures which can be used in the process include those in the range of above about atmospheric to about 500 psig or higher. It is preferred to use pressures below 500 psig. in order to reduce the cost of equipment. Higher pressure operations do not appear to affect the selectivity to a measurable amount. Desorption conditions include the same range of temperatures, pressures as described for adsorption operations. The desorption of the selectively adsorbed isomer can be effected at reduced pressures or elevated temperatures or both. Vacuum purging of an adsorbent to remove the adsorbed isomer from the adsorbent contemplated as a desorption step in the process.

The overall operations taking place can be either batch, or continuous fixed-bed or moving bed systems. In the batch operating processes the feed stock is passed into an adsorbent chamber for a predetermined period of time after which the feed is stopped and any remaining feed present between the adsorbent particles can be purged out of the chamber. A desorbent material may then be passed into the chamber to help remove the adsorbed isomer from the adsorbent. In the continuous fixed bed or moving bed processes the adsorption and desorption operations are continually taking place which allow continuous production of a concentrated feed component and the continual use of feed and desorbent streams.

In adsorptive-separation processes an important factor that is used to determine the ability of a particular adsorbent to separate components of a feed is the selectivity of the adsorbent for one component as compared to another component. The selectivity, B, as used throughout this specification is defined as the ratio of two components of the adsorbed phase over the ratio of the same two components in the unadsorbed phase at equilibrium conditions and is expressed in equation form in equation (5) below, $$\text{Selectivity} = B_{C/D} = \frac{(\text{Vol\% } C/\text{Vol\% } D)_A}{(\text{Vol\% } C/\text{Vol\% } D)_U} \quad (5)$$

where C and D are two components of the feed represented in volume percent and the subscripts A and U represent the adsorbed and unadsorbed phases respectively. The equilibrium conditions as defined here were determined when the feed passing over a bed of adsorbent did not change composition after contacting the bed of adsorbent, or in other words, there was no net transfer of material occurring between the unadsorbed and adsorbed phases when the selectivity of the two selected components was measured.

As can be seen when the selectivity of two components approaches unity there is no preferential adsorption of one component by the adsorbent. As the absolute value of B becomes greater than unity there is a preferential selectivity by the adsorbent of one component. When comparing the selectivity of component C over component D, a B larger than unity indicates preferential adsorption of component C within the adsorbent while a B less than unity would indicate that component D is preferentially adsorbed leaving an unadsorbed phase richer in component C and adsorbed phase richer in component D.

EXAMPLE I

In this experiment a test was performed in a manner to evaluate an adsorbent's ability to separate cymene isomers. The absorbent was a type X structured zeolite which contained a small portion of binder material. It was ion-exchanged with both barium and potassium to give a zeolite which contained about four times the weight percent of barium oxide as compared to potassium oxide. There was less than about 1 wt.% of the zeolite which contained the native sodium. The adsorbent was dried to a predetermined water level before it was utilized in the process.

The adsorbent was placed in an elution column which was maintained at about 150° C. with moderate pressures during the entire operations. The column was connected to a gas chromatograph which measured the cymenes as they were desorbed from the adsorbent. Using the data from the chromatograph it was possible to determine the degree of selectivity of the adsorbent for various cymene isomers.

The feed stock utilized was made up of about 20 vol.% of mixed cymenes, 5 vol.% of normal $C_9$ paraffin which was used as a tracer and 75 vol.% toluene. The mixed cymenes contained about 66.4% meta-cymene, 30.5% paracymene, and 3.1% ortho-cymene. The desorbent was 100% toluene. A 10 cc. pulse of a feed mixture was injected into the column of adsorbent and then desorbed with the toluene desorbent. The desorbent rate was 1 cc. per minute which caused peak envelopes to be eluted from the column. The envelopes were evaluated using standard techniques. The evaluation procedures were found to accurately reproduce the pulse testing results into relative selectivity data. Reproducible data from the above experiments showed that cymene separation was feasible using this type of an adsorbent. The average relative selectivities for cymene isomers are shown in Table I below.

TABLE I

| Cymene Separation | |
|---|---|
| $B_{p/m}$ | 3.2 |
| $B_{p/o}$ | 2.5 |

The selectivities shown above show that it is possible to separate the para-isomer from a mixture thereof para, meta and ortho-cymenes because the adsorbent is selective towards para with respect to both the meta and ortho-cymene isomers.

EXAMPLE II

In experiments using an apparatus similar to that described previously for a fixed-bed continuous countercurrent separation operation, diethylbenzenes were separated using a type X structured zeolite containing barium and potassium ion exchanged upon the zeolite. The feed stream used in this example consisted of a mixture of diethylbenzenes made up of 26.3 wt.% para-diethylbenzene, 59.1 wt.% meta-diethylbenzene, 8 wt.% ortho-diethylbenzene, 3.6 wt.% normal butylbenzene and 3.0 wt.% iso butyl benzene. The process was operated in the liquid phase at about 200 psig. and a constant temperature of 350° F. Toluene was used as a desorbent.

During normal operations approximately 90.7% of the para-diethylbenzene fed to the process was recovered as an extract stream which contained approximately 99.7% para-diethylbenzene as compared to other $C_{10}$ aromatic hydrocarbons. This example indicated that para-diethylbenzene could be separated using a barium-potassium exchanged zeolite. By changing the cations placed on the zeolite it would be possible to selectively adsorb meta- or ortho-diethylbenzene isomers.

EXAMPLE III

In this experiment, type X and type Y zeolites were exchanged with various cations to determine the selectivity of the adsorbents for para-isomers as compared to meta-and ortho- isomers of a bialkyl-substituted aromatic hydrocarbon. The tests were performed on alkyl aromatics including diethylbenzenes, cymenes, and xylenes. The absorbents contained essentially pure type X or type Y zeolite with the exception of the type X zeolite which contained a small portion of the binder material to hold it together. The adsorbents were approximately 20-40 mesh particle size.

The adsorbents which contained a single cation were essentially totally ion exchanged and generally contained less than about 2 wt.% residual sodium on a volatile free basis. The volatile free basis of less than 2 wt.% residual sodium on the adsorbent was measured after it had been subjected to 900° calcination temperatures to drive off most of the volatile material contained within the adsorbent. The adsorbents which contained two different cations were also totally ion-exchanged and contained less than about 2 wt.% residual sodium on a volatile free basis. The adsorbents containing two cations, contained approximately equal percentages of the cationic exchange sites in the zeolite occupied by the individual cations.

In determining the selectivities it has been found from previous experience when the mixture of para-, meta- and ortho-isomers are passed into a testing unit that the analysis procedure is complicated by the fact that three isomers are present. Consequently, in order to reduce the difficulty of analysis and determination of the selectivities the ortho-isomer was omitted from the feedstock. From previous experiments it has been found that the meta- and ortho- behave in substantially the same manner so that a sieve which selectively adsorbs a meta-isomer as compared to a para-isomer will in almost all instances also selectively adsorb the ortho- isomer as compared to para-isomer. The separation of meta- and ortho-isomers is very difficult and for the purposes of our experiment was considered to be not feasible. The results of the experimental separation of para-isomers from meta-isomer are shown in Table II below:

TABLE II

| Zeolite Type | Cation(s) Present | Selectively Adsorbed Isomer (s) |
|---|---|---|
| Y | K | Para |
| Y | Rb | Para |
| Y | Cs | Para |
| Y | Ag | Para |
| Y | Ba | Para |
| X | Na | Para |
| Y | Li | Meta and Ortho |
| Y | Na | Meta and Ortho |
| Y | Be | Meta and Ortho |
| Y | Mg | Meta and Ortho |
| Y | Ca | Meta and Ortho |
| Y | Sr | Meta and Ortho |
| Y | Mn | Meta and Ortho |
| Y | Cd | Meta and Ortho |
| Y | Cu | Meta and Ortho |

TABLE II-continued

| Zeolite Type | Cation(s) Present | Selectively Adsorbed Isomer (s) |
|---|---|---|
| Y | K, Ba | Para |
| Y | K, Be | Para |
| Y | K, Mg | Para |
| Y | K, Rb | Para |
| Y | K, Cs | Para |
| Y | Rb, Ba | Para |
| Y | Cs, Ba | Para |
| X | K, Ba | Para |
| Y | K, Cu | Para |
| Y | Cu, Cd | Meta and Ortho |
| Y | Cu, Ag | Meta and Ortho |
| Y | Zn, Ag | Meta and Ortho |

As can be seen above, various cations allow the para-isomer to be selectively adsorbed over the meta and ortho isomers while in other instances the meta and ortho isomers are selectively adsorbed as compared to the para-isomer.

We claim as our invention:

1. A process for separating bi-alkyl substituted monocyclic aromatic isomers having more than eight and less than about eighteen carbon atoms per molecule from a feed mixture containing at least two of said isomers including the para-isomer which comprises contacting said feed with a crystalline aluminosilicate selected from the group consisting of type X structured and type Y structured zeolites containing at cationic exchangeable sites both barium and potassium cations, or potassium and beryllium cations, or potassium and magnesium cations, or rubidium and barium cations, or cesium and barium cations, or potassium and rubidium cations or potassium and cesium cations, said contacting being at adsorption conditions to selectively adsorb said para-isomer from said feed.

2. claim 1 further characterized in that said crystalline aluminosilicate contains barium and potassium cations at cationic exchangeable sites within said zeolite.

3. claim 1 further characterized in that said feed mixture contains diethylbenzene isomers and that para-diethylbenzene is selectively adsorbed.

4. claim 1 further characterized in that said feed mixture contains cymene isomers and that para-cymene is selectively adsorbed.

5. A process for separating cymene isomers from a feed mixture consisting essentially of p-cymene and m-cymene, which comprises contacting said mixture with a type X structured zeolite containing at cationic exchangeable sites both barium and potassium cations, said contacting being at adsorption conditions to selectively adsorb said p-cymene from said mixture.

* * * * *